United States Patent [19]

Okuda

[11] 3,955,575

[45] May 11, 1976

[54] DIAPER

[76] Inventor: Yoshizo Okuda, 3-16 Gakuenkita 1-chome, Nara, Japan

[22] Filed: Dec. 13, 1974

[21] Appl. No.: 532,607

[52] U.S. Cl. ............................................. 128/284
[51] Int. Cl.² ........................................ A61F 13/16
[58] Field of Search............ 128/284, 287, DIG. 15; 66/194

[56] References Cited
UNITED STATES PATENTS

| | | | |
|---|---|---|---|
| 1,329,619 | 2/1920 | McNair | 128/284 |
| 2,827,052 | 3/1958 | Goodman et al. | 128/284 |
| 3,057,353 | 10/1962 | Casale | 128/284 |
| 3,367,333 | 2/1968 | Scheier | 128/284 |
| 3,653,381 | 4/1972 | Warnken | 128/284 |

*Primary Examiner*—Lawrence W. Trapp
*Attorney, Agent, or Firm*—Eric P. Schellin; John E. Becker

[57] ABSTRACT

A diaper of tubular knitted form having a pile surface on the outside of the tubular body and a smooth surface on its inside. The upper half portion of the tubular diaper has a larger width than its lower half portion. The diaper is less bulky, has higher water-absorbing properties and feels softer than conventional diapers and is therefore especially suitable for use by growing babies and infants.

33 Claims, 19 Drawing Figures

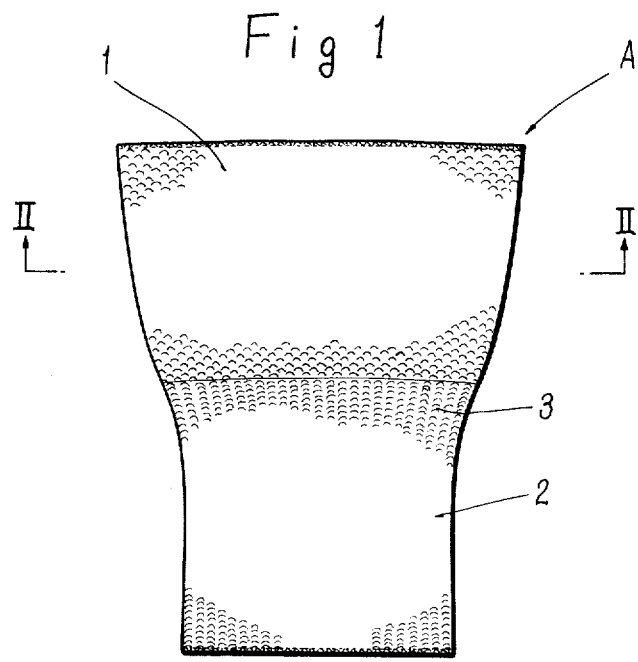
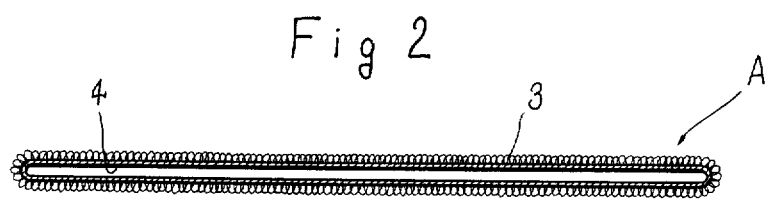
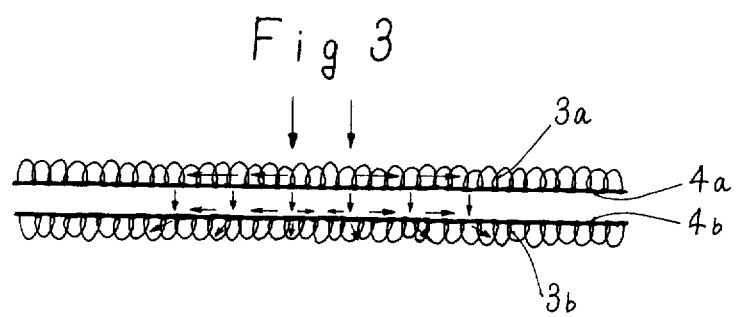

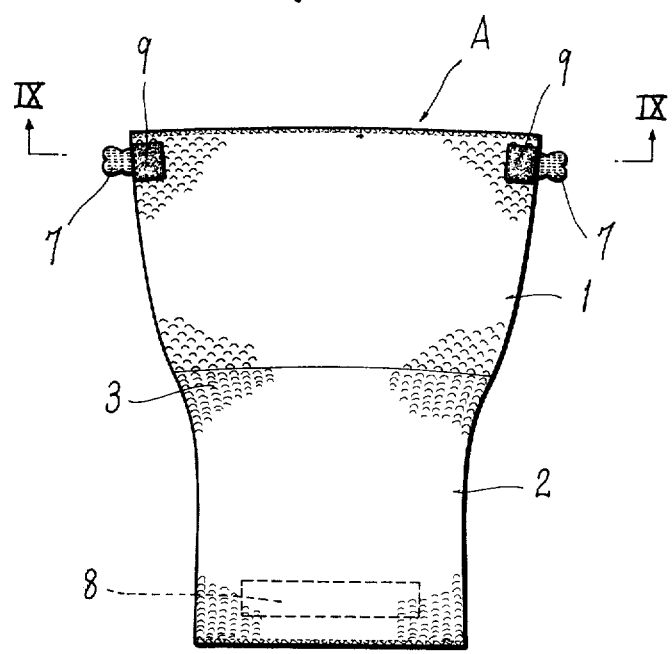
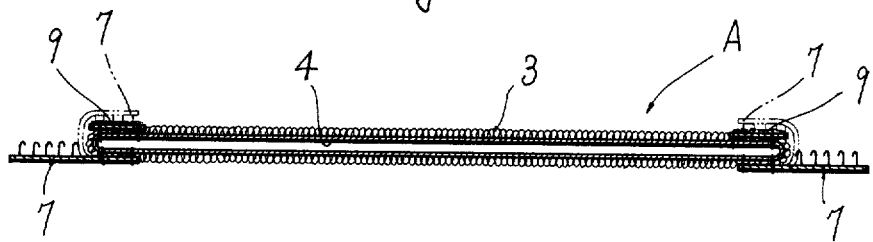

3,955,575

DIAPER

BACKGROUND OF THE INVENTION

The present invention relates to diapers for babies and infants, more particularly to a diaper knitted in the form of a tube having a pile surface on the outside of the tube and a smooth surface on the inside thereof.

Diapers to be worn by rapidly growing babies and infants must permit free physical movement, be comfortable to wear without undue tightness, and must not injure or irritate the soft skin. It is further essential that they have high water-absorbing properties. Conventional diapers, however, fail to completely fulfill all of these requirements whether they are made of fabric or paper. The known prior art diapers of which I am aware have the disadvantages of being bulky, low in stretchability and uncomfortable to wear. Moreover they do not have sufficiently high water-absorbing properties.

SUMMARY OF THE INVENTION

The aforementioned disadvantages are eliminated by the diaper of this invention which is knitted in the form of a tube having a pile surface on the outside of the tube and a smooth surface on the inside thereof.

An object of this invention is to provide a tubular knitted diaper having high stretchability and comfortable wear characteristics.

Another object of this invention is to provide a diaper which has a soft pile surface on its outside which is especially comfortable to the skin, and which is highly water-absorbent.

Another object of this invention is to provide a diaper having an upper half portion of a relatively large width and which is capable of fully wrapping the backside, crotch, abdomen and flanks of the baby or infant.

Another object of this invention is to provide a diaper having a more padded or bulky center portion so as to increase the absorbing properties of the diaper.

Another object of this invention is to provide a diaper which has complementary engageable fastener pieces preferably of the Velcro or Magic Tape type embodying patches of coacting miniature hooks and loops formed of relatively rigid filament material for fastening the diaper on the infant, and which is therefore adjustable to accommodate babies of different size and to allow for body growth of the baby or infant.

These and other objects of this invention will become more apparent from the following detailed description together with the illustrative accompanying drawings.

BRIEF DESCRIPTION OF THE DRAWINGS

FIG. 1 is a plan view showing one embodiment of the diaper of this invention in open flat condition;

FIG. 2 is an enlarged cross-sectional view taken along the line II—II in FIG. 1;

FIG. 3 is a fragmentary enlarged view of FIG. 2 to show the relationship between the knitted structure of the diaper and the flow of urine discharged from the baby;

FIG. 8 is a plan view showing a diaper having cooperative engageable fastening means;

FIG. 9 is an enlarged cross-sectional view taken along the line IX—IX in FIG. 8;

DESCRIPTION OF THE PREFERRED EMBODIMENTS

With reference to FIGS. 1 to 3, a diaper generally designated A has the form of a knitted tube, shown in the flattened open condition, and having an upper half portion 1 of a relatively larger width than the lower half portion 2, as shown. The tubular diaper A has a pile surface 3 on its outside and a smooth surface having no pile on its opposing inner surfaces.

The diaper A is knitted usually by a circular knitting machine using cottom yarns such as 30s combed yarn. Alternatively, the diaper A may be knitted of 85% of cotton yarns as mentioned above and combined with 15% of (for example 75-denier) special finished yarns of synthetic fibers. Such latter fibers may include crimped nylon yarns which preferably have a high degree of curliness or are precrinkled sufficiently to impart a predetermined resiliency or stretchability to the garment or diaper. The crinkled character of the synthetic yarns is important in greatly facilitating the diffusing of the urine over a wider area and within the inner tubular portions.

The various yarns are made so that a soft pile surface is provided on the outside of the diaper, with the pile being made only from cotton yarns in a most preferred embodiment, and as to form smooth opposing inner surfaces from combinations of the two types of yarns.

Further, by having the upper half portion 1 knitted using any suitable form of a highly stretchable pile stitch structure, such as "kanoko" fabric or tuck stitch, and the lower half portion 2 made with only a plain-knitted pile stitch structure, the upper half portion will have a larger width than the lower half portion.

Figure 12:
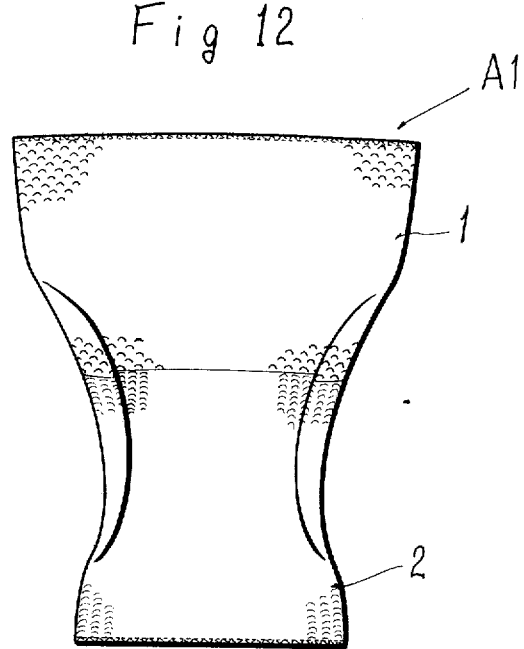
FIGS. 12 to 14 are views showing the progressive folding use of the diaper of FIG. 1.
Figure 13:
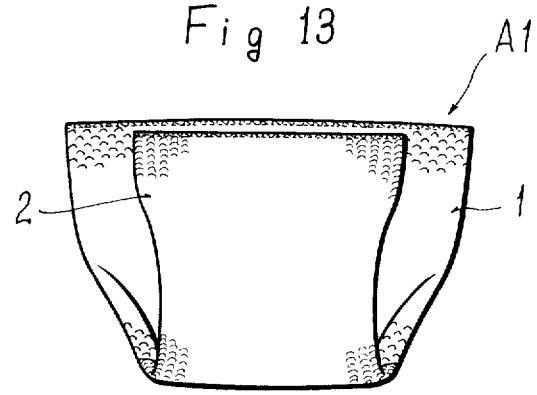
Figure 14:
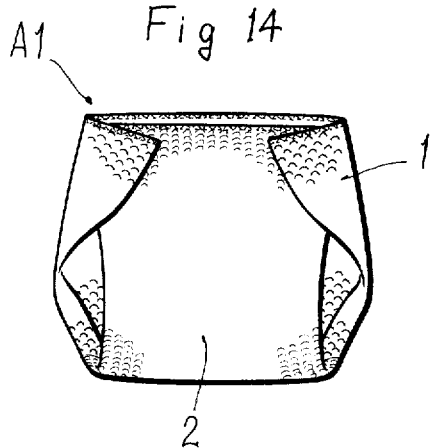

To use the diaper, the opposite side edges of its lower half portion are folded inward to narrow that portion in conformity with the crotch of the baby (see FIG. 12), and the baby's bottom is placed on the upper half portion of the diaper. The lower half portion is then drawn up between the legs and placed over the abdomen (FIG. 13). Subsequently, the upper opposite side parts of the upper half portion are slightly stretched and fitted around the flanks of the baby so as to preferably overlay lateral side portions of the upturned lower portion, as shown in FIG. 14.

The present improved diaper, being in the form of a tubular knitted fabric, is highly stretchable in its entirety and has an excellent ability to return to its original shape, thereby providing a snug fit around the baby. Because the upper half portion of the diaper has a larger width than the lower half portion, the backside, crotch, abdomen and flanks can be fully wrapped with one diaper. Accordingly, it is extremely low in bulkiness during use, thereby lessening the load on the abdomen, and permits free bodily motion without imparting an uncomfortably tight feel to the body. With the pile surface adapted to contact the skin, the diaper is especially soft and comfortable to wear and well-suited for new babies.

Figure 5:
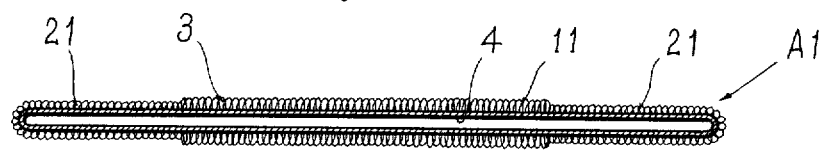
FIG. 5 is an enlarged cross-sectional view taken along the line V—V in FIG. 4.

Inasmuch as the tubular diaper has an outside pile surface made of water-absorbent cotton yarns, and smooth opposing inner surfaces having no pile, the urine discharged is first absorbed by the pile surface 3a, (FIG. 3) and the remainder of the liquid is diffused over and absorbed by the smooth inner surface 4a. Excess liquid is then absorbed by the opposing smooth surface 4b while being diffused thereover and is ultimately absorbed by the highly absorbent pile surface 3b, as illustrated in FIG. 5. In this way, the diaper can absorb liquid very efficiently over a much wider area, thereby preventing local seepage experienced with the more conventional prior art diapers. An apparent advantage is the elimination or marked reduction of wetting of clothes and bedding. It is therefore more sanitary to use.

When the diaper A is knitted of a combination of cotton yarns and special finished yarns of synthetic fibers having high curliness such as nylon yarns, wherein the outer pile surface is made of only the cotton yarns, and the smooth inner surface is made of both the cotton and special finished yarns in mixture, the smooth inner surface, by having relatively low water-absorbing properties, permits water to diffuse over a still wider area to greatly improve the water-absorbing properties of the diaper. Moreover, the combination of pre-crinkled or pre-curled synthetic fibers and natural cotton fibers serves to provide the finished diaper fabric with pleasantly soft character which it retains even after repeated washings.

Figure 4:
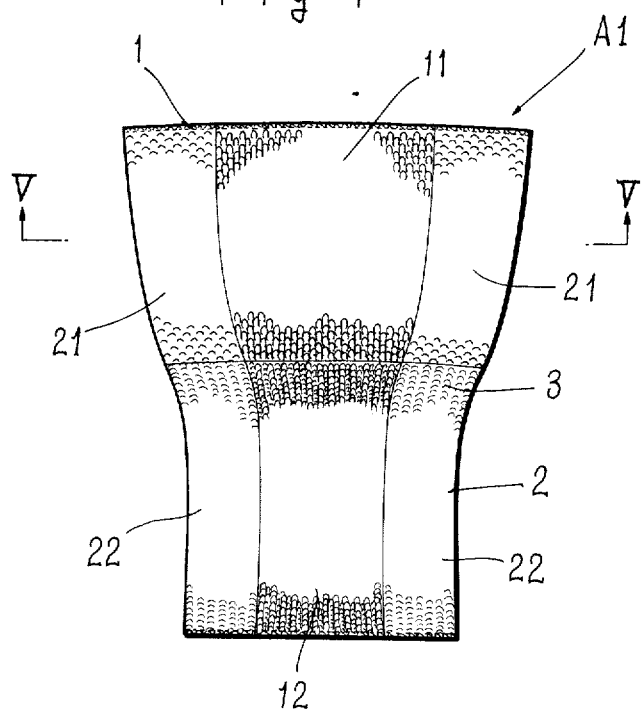
FIG. 4 is a plan view similar to FIG. 1, and showing another embodiment of the flattened diaper which has a bulky center portion.

FIGS. 4 and 5 show a diaper A1 in which the longitudinal center back and front parts, 11 and 12 respectively, of the upper and lower half portions are made bulkier than the respective opposite side portions 21, 21 and 22, 22. When knitting the diaper, yarns are supplied in larger amounts to the center parts than to the side portions to lengthen the piles and to thereby increase bulkiness. For example, loops in center parts are about 2-mm long, while those in the side portions are about 1-mm long. The diaper thus made has improved water-absorbing properties.

Figure 6:
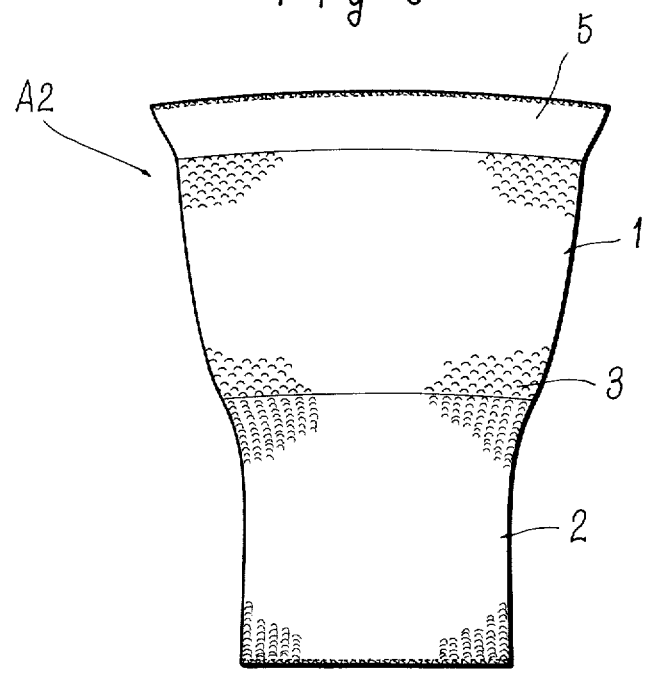
FIG. 6 is a plan view showing another embodiment having an auxiliary piece extending upwardly and laterally from the upper end of the diaper body.
Figure 7:
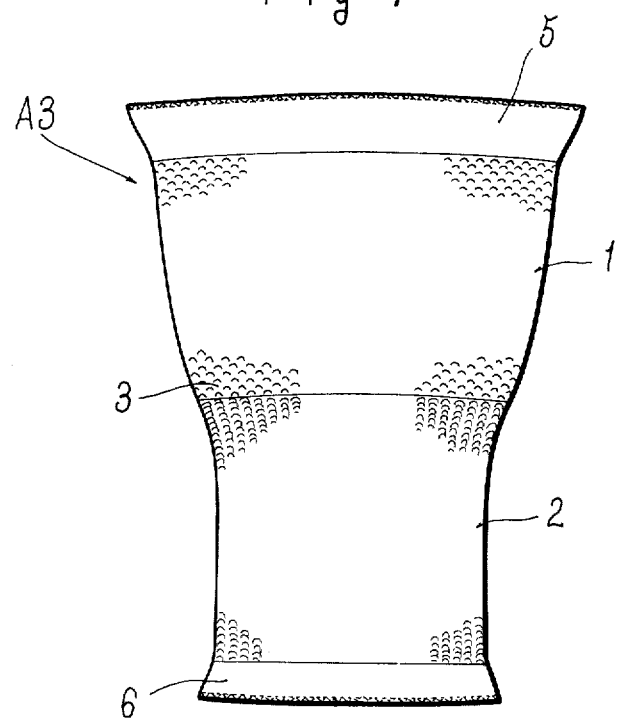
FIG. 7 is a plan view similar to FIG. 6 showing still another embodiment having auxiliary pieces attached to the upper and lower ends of the diaper respectively.

FIG. 6 shows a diaper A2 having an auxiliary piece 5 extending continuously from and along the upper edge of the diaper. The diaper A3 shown in FIG. 7 is very similar to the diaper A2 in FIG. 6, having the same upper auxiliary piece 5, plus a further auxiliary piece 6 extending from the illustrated lower end of the diaper. These modified diapers can have the auxiliary edge pieces readily sewn onto the body of the diaper in a manner so as to prevent the upper or lower ends from fraying. These auxiliary pieces are helpful for fully wrapping the flanks of the baby.

Figure 10:
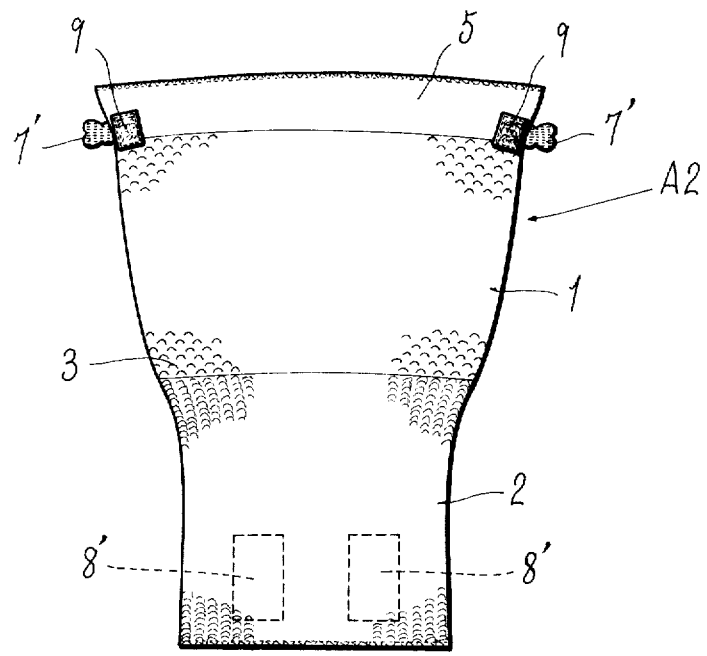
FIGS. 10 and 11 are plan views respectively showing further modified examples or arrangements of the cooperatively engageable fastening means.

FIGS. 8 to 11 show diapers of the type of FIGS. 1 and 6, having engageable fastening means attached thereto. The engageable fastening means are preferably of a special textile or cloth type, such as those commercially known as VELCRO or MAGIC TAPE. Such fasteners comprise a plurality of miniature hook pieces 7 secured to a fabric patch which has a portion thereof attached to the rear surface of the upper portion of the diaper A at its opposite edges. The hooks are operatively engageable with a patch of complementary loop pieces 8, attached to the rear surface of the diaper approximately at its lower end, to effect fastening of the diaper during use. A strip of the loop-bearing material 8 may be horizontally attached to the diaper, as per FIG. 8, or a pair of generally vertically elongated rectangular patches of the loop pieces 8' may be attached, as shown in FIG. 10, to the left and right side portions of the diaper. The hook-bearing pieces are designated 7' in FIG. 10.

Figure 11:
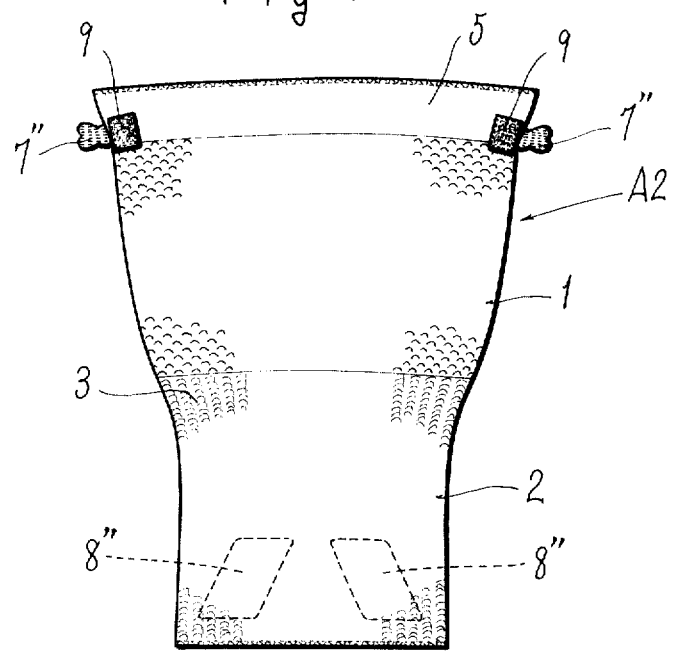
Figure 16:
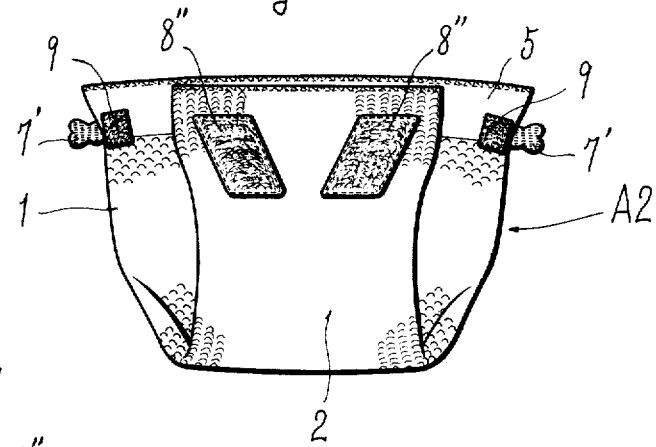

Alternatively, as shown in FIG. 11, vertically elongated, obliquely disposed, parallelogrammatic patches of the loop pieces 8'' may be attached to the diaper, such that the upper and lower sides of each patch 8'' are positioned horizontally with the corresponding sides of the other. In this form, the hook-bearing patches or pieces 7'' are selectively displaceable from one position to another upon the loop-bearing pieces 8'' so as to be movable obliquely outward thereof, as seen in FIG. 16. The pieces 8'', therefore, are affixable in a suitable position in accordance with the growth of the baby, for example in accordance with 6-month-old, 12-month-old, 18-month-old and 24-month-old stages and at intermediate stages thereof. In this way, the effective length and girth of the diaper A are fully adjustable.

Figure 15:
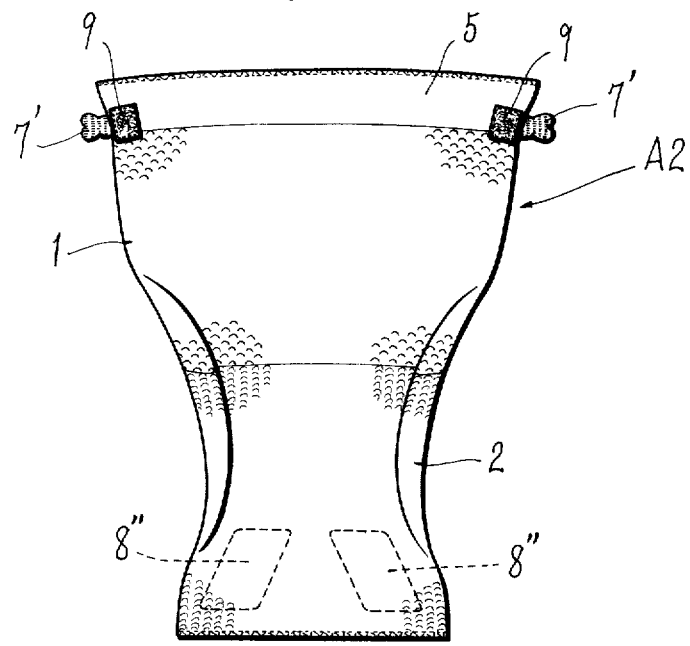
FIGS. 15 to 17 are views similar to FIGS. 12 – 14 showing features of the progressive adjustability and folded up use of the diaper of FIG. 11.
Figure 17:
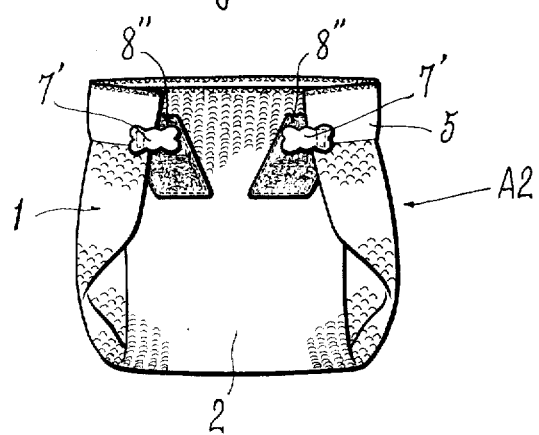

FIGS. 15 – 17 show not only the progressive folding steps of the diaper type A2, but also the selective adjustability features afforded by the unique dispositioning of the fastener means 7 and 8.

As shown in FIG. 8 – 11 and 15 – 19, additional patches of loop-bearing pieces designated at 9 are attached to one surface of the diaper opposite to the position where the hook-bearing pieces 7 (or 7' and 7'') are attached. When washing or replacing the diaper, the hook-bearing pieces are folded over and fixed to these loop pieces, as indicated in dot-and-dash line in FIG. 9, so that the hook pieces will not engage with other articles or tend to injure the skin.

Figure 18:
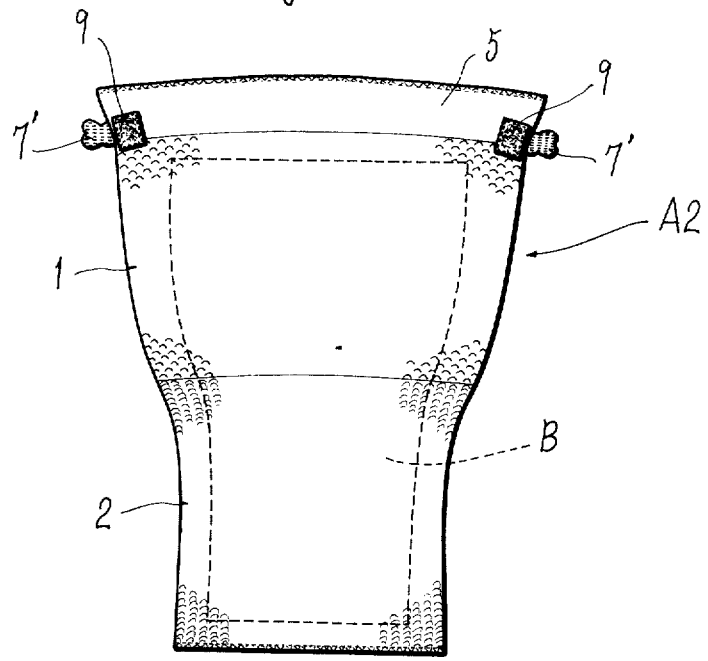
FIG. 18 is a plan view showing a modification wherein the diaper of FIG. 11 has embodied therewith an auxiliary diaper inserted therein.
Figure 19:
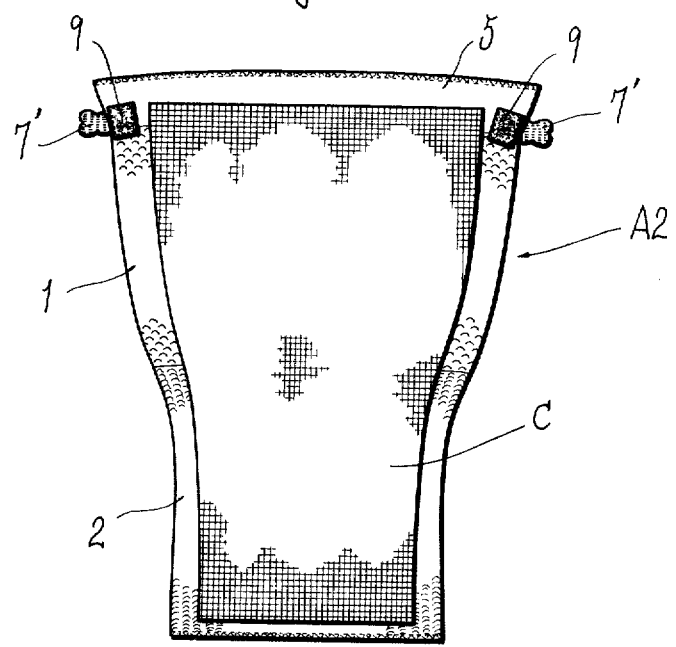
FIG. 19 is a plan view showing the diaper of FIG. 11 on which a net is placed for use therewith.

The present invention is further characterized in that an auxiliary diaper B indicated in dotted outline in FIG. 18 is either placed over or inserted into any of these improved tubular diapers for use during night when a larger amount of urine is likely to be discharged. The auxiliary diaper B is proportionately smaller than the diaper A. The assembled or doubled diaper will then have improved water-absorbing properties. Further, if a net C (FIG. 19), having no water-absorbing properties and which is permeable to water, is placed over the diaper for use in combination therewith, the diaper will be very easy to wash after defecation.

The knitted structure of the diaper A of this invention is not particularly limited. A fabric of usual pile stitch, stretchable tuck stitch such as kanoko fabric or any suitable construction is usable. Also complementary patches 7 and 8 for fastening the diaper may be reversed, if desired, and/or less desirably replaced by suitable other fastener means.

While specific embodiments of this novelly improved diaper have been shown and described, other variations and modifications may suggest themselves to those skilled in the art without departing from the spirit of the invention and the scope of the appended claims.

What is claimed is:

1. A textile cloth diaper comprising
a body of tubular knitted form adapted to lay flat in open ready-to-use condition thereby providing two substantial plies for the body;
said body having upper and lower generally half portions, of which said upper half portion is of greater lateral width than said lower half portion;
said body being comprised of a combination of cotton and at least one other special finished synthetic fiber;
said cotton and synthetic fibers being so combined and arranged so that said tubular body has an integral, soft, pile-covered outer surface of cotton fibers only, and smooth pile-free inner surfaces, the latter constituted by two adjacently opposed plies having substantially contiguous smooth inner surfaces when in said flat ready-to-use condition.

2. The diaper of claim 1, wherein said body has a longitudinal central portion whose upper and lower portions thereof have an integral knitted construction providing pronounced increased thickness or bulk than the laterally opposite side portions.

3. The diaper of claim 2, wherein said diaper body is provided with an auxiliary pile-free extension piece unitarily attached to and coextensive with an upper end of said diaper.

4. The diaper of claim 3, wherein said diaper body is provided also with an auxiliary pile-free extension piece continuously along a lower most end of said diaper body.

5. The diaper of claim 1, wherein said upper and lower body portions are integrally interconnected by an intermediate portion having gradually tapered laterally opposite side portions.

6. The diaper of claim 1, wherein said body in said flat ready-to-use condition has a forward face-up surface and a rearward face-down surface, to the latter surface of which are attached at upper opposite lateral side portions and at a lower portion of said same face complementary coacting fastener means by which said diaper portions are held in interconnected folded-in-use condition.

7. The diaper of claim 6, wherein said complementary coacting fastener means are coating pieces of different character known commercially as a VELCRO or MAGIC TAPE type material, wherein said pieces of the material are of a size and shape and strategically placed so as to provide a variable range of quick attachment and detachment to accommodate different size growing babies.

8. The diaper of claim 7 wherein
said body has provided on said rearward face-down surface relatively short strips of said fastener piece material of one character attached at said opposite lateral side portions in a working face-up condition, and which have free end portions projecting beyond lateral side portions of the diaper body;
said body also having attached thereto on its said forward face-up surface at generally opposite points of attachment of said strips of material, separate pieces of material of a different but complementary coacting character from said firstmentioned strips, and in a working face-up condition to thereby facilitate removable temporary inter-connection of the free ends of said first-mentioned strips with the second-mentioned separate pieces of different but complementary coacting character as during washing of the diaper and other non-applied uses thereof.

9. The diaper of claim 6, wherein said complementary fastener means include a strip of a first character laterally projecting from each of said laterally opposite side portions, and a spaced-apart pair of fastener pieces of a complementary coacting second character, said latter-mentioned pieces being generally vertically elongated to provide a predetermined range of adjustment for interrelated fastening of said upper and lower body portions when in folded-in-use condition.

10. The diaper of claim 9, wherein said latter-mentioned generally vertically elongated pieces of a second character have essentially a parallelogram shape with upper and lower edges of each piece disposed generally horizontal and in parallel to a generally horizontal upper edge of said diaper body; and
said parallelogram shaped pieces having inclined intermediate opposite side edges and disposed with said side edges slanting obliquely outwardly toward said lateral side edges, thereby providing both length and girth adjustment features for the diaper.

11. The diaper of claim 10, wherein said diaper body is provided with an auxiliary pile-free extension piece unitarily attached to and coextensive with an upper end of said diaper.

12. The diaper of claim 11, wherein said auxiliary piece has oppositely lateral edges tapering from a greater extent at the top to a lesser extent equal to the lateral width of said upper portion of said diaper.

13. The diaper of claim 1, wherein said diaper body is provided with an auxiliary pile-free extension piece unitarily attached to and coextensive with an upper end of said diaper.

14. The diaper of claim 13, wherein said auxiliary piece has oppositely lateral edges tapering from a greater extent at the top to a lesser extent equal to the lateral width of said upper portion of said diaper.

15. The diaper of claim 13, wherein said diaper body is provided also with an auxiliary pile-free extension piece continuously along a lower-most end of said diaper body.

16. The diaper of claim 11, wherein said diaper body is provided also with an auxiliary pile-free extension piece continuously along a lower most end of said diaper body.

17. The diaper of claim 10, and further including an auxiliary separate diaper having a similar but proportionately smaller overall body size, disposable within said tubular body of the first-mentioned principal diaper.

18. The diaper of claim 10, further including in association with its said forward face-up surface adapted for engagement against a baby's bottom, a water-pervious piece of open mesh netting material not exceeding the overall size of said diaper body.

19. The diaper of claim 1, wherein said synthetic fiber consists of crimped nylon yarns having a high degree of precrinkled curliness as to impart a predetermined resiliency, stretchability, and pleasantly soft character to the diaper which is retained therein even after repeated washings.

20. The diaper of claim 19, wherein said body has a longitudinal central portion whose upper and lower portions thereof have an integral knitted construction providing pronounced increased thickness or bulk than the laterally opposite side portions; and wherein said body in said flat ready-to-use condition has a forward face-up surface and a rearward face-down surface, to the latter surface of which are attached at upper opposite lateral side portions and at a lower portion of said same surface, complementary coacting fastener means by which said diaper portions are held in interconnected folded-in-use condition.

21. The diaper of claim 20, wherein said complementary coacting fastener means are coating pieces of different character known commercially as a VELCRO or MAGIC TAPE type material, wherein said pieces of the material are of a size and shape and strategically placed so as to provide a variable range of quick attachment and detachment to accomodate different size growing babies.

22. The diaper of claim 21 wherein
said body has provided on said rearward face-down surface relatively short strips of said fastener piece material of one character attached at said opposite lateral side portions in a working face-up condition, and which have free end portions projecting beyond lateral side portions of the diaper body;
said body also having attached thereto on its said forward face-up surface at generally opposite points of attachment of said strips of material, separate pieces of material of a different but complementary coacting character from said first-mentioned strips, and in a working face-up condition to thereby facilitate removable temporary inter-connection of the free ends of said first-mentioned strips with the second-mentioned separate pieces of different but complementary coacting character as during washing of the diaper and other non-applied uses thereof.

23. The diaper of claim 20, wherein said complementary fastener means include a strip of a first character laterally projecting from each of said laterally opposite side portions, and a spaced-apart pair of fastener pieces of a complementary coacting second character, said latter-mentioned pieces being generally vertically elongated to provide a predetermined range of adjustment for interrelated fastening of said upper and lower body portions when in folded-in-use condition.

24. The diaper of claim 23, wherein said latter-mentioned generally vertically elongated pieces of a second character have essentially a parallelogram shape with upper and lower edges of each piece disposed generally horizontal and in parallel to a generally horizontal upper edge of said diaper body; and
said parallelogram shaped pieces having inclined intermediate opposite edges and disposed with said side edges slanting obliquely outwardly toward said lateral side edges, thereby providing both length and girth adjustment features for the diaper.

25. The diaper of claim 24, wherein said diaper body is provided with an auxiliary pile-free extension piece unitarily attached to and coextensive with an upper end of said diaper.

26. The diaper of claim 25, wherein said auxiliary piece has oppositely lateral edges tapering from a greater extent at the top to a lesser extent equal to the lateral width of said upper portion of said diaper.

27. The diaper of claim 19, wherein said diaper body is provided with an auxiliary pile-free extension piece unitarily attached to and coextensive with an upper end of said diaper.

28. The diaper of claim 27, wherein said auxiliary piece has oppositely lateral edges tapering from a greater extent at the top to a lesser extent equal to the lateral width of said upper portion of said diaper.

29. The diaper of claim 27, wherein said diaper body is provided also with an auxiliary pile-free extension piece continuously along a lower-most end of said diaper body.

30. The diaper of claim 25, wherein said diaper body is provided also with an auxiliary pile-free extension piece continuously along a lowermost end of said diaper body.

31. The diaper of claim 24, and further including an auxiliary separate diaper having a similar but proportionately smaller overall body size, disposable within said tubular body of the first-mentioned principal diaper.

32. The diaper of claim 24, further including in association with its said forward face-up surface adapted for engagement against a baby's bottom, a water-pervious piece of open mesh netting material not exceeding the overall size of said diaper body.

33. The diaper of claim 26 further including an auxiliary separate diaper having a similar but proportionately smaller overall body size, disposable within said tubular body of the first-mentioned principal diaper; and also further including in association with its said forward face-up surface adapted for engagement against a baby's bottom, a water-pervious piece of open mesh netting material not exceeding the overall size of said diaper body.

* * * * *